(12) United States Patent
Li et al.

(10) Patent No.: US 12,064,268 B2
(45) Date of Patent: Aug. 20, 2024

(54) SYSTEMS AND METHODS FOR MEDICAL IMAGING

(71) Applicant: SHANGHAI UNITED IMAGING HEALTHCARE CO., LTD., Shanghai (CN)

(72) Inventors: Wei Li, Shanghai (CN); Yongqin Xiao, Shanghai (CN); Ziyan Wu, Cambridge, MA (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 200 days.

(21) Appl. No.: 17/203,733

(22) Filed: Mar. 16, 2021

(65) Prior Publication Data
US 2021/0290166 A1  Sep. 23, 2021

(30) Foreign Application Priority Data

Mar. 17, 2020  (CN) .......................... 202010185201.9
Mar. 19, 2020  (CN) .......................... 202010196081.2

(51) Int. Cl.
| A61B 5/00 | (2006.01) |
| A61B 5/11 | (2006.01) |
| A61B 5/113 | (2006.01) |

(52) U.S. Cl.
CPC ............. *A61B 5/70* (2013.01); *A61B 5/0033* (2013.01); *A61B 5/1116* (2013.01); *A61B 5/113* (2013.01); *A61B 5/4504* (2013.01); *A61B 5/7285* (2013.01)

(58) Field of Classification Search
None
See application file for complete search history.

(56) References Cited

U.S. PATENT DOCUMENTS

| 6,094,468 A | 7/2000 | Wilting et al. |
| 7,054,412 B2 | 5/2006 | Scheuering |
| 2007/0053503 A1 | 3/2007 | Zelnik et al. |
| 2016/0220844 A1 | 8/2016 | Paysan et al. |

(Continued)

FOREIGN PATENT DOCUMENTS

| CN | 104068886 A | 10/2014 |
| CN | 106361364 A | 2/2017 |

(Continued)

OTHER PUBLICATIONS

The Extended European Search Report in European Application No. 21162996.9 mailed on Jul. 30, 2021, 9 pages.

(Continued)

*Primary Examiner* — Joel Lamprecht
*Assistant Examiner* — Ashish S Jasani
(74) *Attorney, Agent, or Firm* — METIS IP LLC

(57) ABSTRACT

A method for medical imaging is provided. The method may include automatically determining that a positioning procedure of a subject has been finished based on image data of the subject captured by an image capturing device. The method may also include obtaining status information of a medical device. The method may further include causing the medical device to perform a scan on the subject based on a determination result that the positioning procedure of the subject has been finished, the status information of the medical device, and a starting signal of the scan.

13 Claims, 7 Drawing Sheets

(56) References Cited

U.S. PATENT DOCUMENTS

| | | |
|---|---|---|
| 2018/0150681 A1 | 5/2018 | Wang et al. |
| 2018/0247427 A1* | 8/2018 | Geiger ................. G06T 7/73 |
| 2019/0143145 A1* | 5/2019 | Laurence, Jr. ....... A61N 5/1081 |
| | | 600/1 |
| 2020/0202620 A1* | 6/2020 | Kiely .................. A61B 6/032 |
| 2020/0205766 A1 | 7/2020 | Wu et al. |

FOREIGN PATENT DOCUMENTS

| | | |
|---|---|---|
| CN | 107582085 A | 1/2018 |
| CN | 108324296 A | 7/2018 |
| CN | 108670279 A | 10/2018 |
| CN | 109480882 A | 3/2019 |
| CN | 110197496 A | 9/2019 |
| CN | 110338827 A | 10/2019 |
| CN | 110507349 A | 11/2019 |
| CN | 110897651 A | 3/2020 |
| DE | 102015214369 A1 | 8/2016 |
| JP | 2019030410 A | 2/2019 |
| WO | 2020198870 A1 | 10/2020 |

OTHER PUBLICATIONS

First Office Action in Chinese Application No. 202010196081.2 mailed on Jun. 20, 2022, 18 pages.

* cited by examiner

SYSTEMS AND METHODS FOR MEDICAL IMAGING

CROSS-REFERENCE TO RELATED APPLICATION

This application claims priority to Chinese Patent Application No. 202010185201.9, filed on Mar. 17, 2020, and Chinese Patent Application No. 202010196081.2, filed on Mar. 19, 2020, the contents of each of which are hereby incorporated by reference.

TECHNICAL FIELD

The present disclosure generally relates to medical imaging, and more particularly, relates to systems and methods for controlling medical devices.

BACKGROUND

Medical imaging techniques, such as a magnetic resonance (MR) technique, a computed tomography (CT) technique, or the like, have been widely used for clinical examination and treatment in recent years.

Medical devices (e.g., a digital radiography (DR) device, a CT device, a linear accelerator device, etc.) may be used to scan a subject by emitting radioactive rays (e.g., X-rays, β-rays, γ-rays, etc.) to the subject. Before and/or during the scan of the subject, the medical device needs to be controlled efficiently to improve the efficiency and/or accuracy of the scan. Therefore, it is desirable to provide systems and methods for controlling medical devices in medical imaging.

SUMMARY

According to an aspect of the present disclosure, a method for medical imaging may be provided. The method may include automatically determining that a positioning procedure of a subject has been finished based on image data of the subject captured by an image capturing device. The method may also include obtaining status information of a medical device. The method may further include causing the medical device to perform a scan on the subject based on a determination result that the positioning procedure of the subject has been finished, the status information of the medical device, and a starting signal of the scan.

In some embodiments, the method may include obtaining personal information of the subject. The method may further include determining positioning guidance information based on the personal information of the subject.

In some embodiments, the method may include determining a posture of the subject based on the image data of the subject. The method may further include determining whether the positioning procedure of the subject has been finished based on the personal information and the posture of the subject.

In some embodiments, the method may include determining a reference posture of the subject based on the personal information of the subject. The method may further include determining whether the positioning procedure of the subject has been finished based on a comparison between the posture and the reference posture of the subject.

In some embodiments, the method may include prompting the subject to send the starting signal based on the determination result that the positioning procedure of the subject has been finished.

In some embodiments, the starting signal of the scan may be a trigger signal automatically generated based on a state of the subject.

In some embodiments, the method may include detecting that the subject maintaining a preset posture for a preset time. The method may further include generating the trigger signal.

In some embodiments, the method may include obtaining breathing information of the subject. The method may further include generating the trigger signal based on the breathing information of the subject.

In some embodiments, the method may include determining morphological information of the subject based on the image data of the subject. The method may further include determining one or more values of one or more acquisition parameters of the medical device based on the morphological information of the subject. The scan may be performed based on the one or more values of the one or more acquisition parameters.

In some embodiments, the method may include determining one or more preset values of the one or more acquisition parameters of the medical device based on a region of the subject to be scanned. The method may further include determining the one or more values of the one or more acquisition parameters of the medical device based on the one or more preset values of the one or more acquisition parameters and the morphological information of the subject.

In some embodiments, the method may include determining the morphological information of the subject by processing the image data of the subject using a morphological information determination model.

In some embodiments, the scan may be a stitching scan or a tomography scan. The one or more acquisition parameters of the medical device may include a stitching scan protocol relating to the stitching scan or a tomography scan protocol relating to the tomography scan.

In some embodiments, the morphological information of the subject may include bone joint information of the subject. The method may further include determining the stitching scan protocol based on the bone joint information of the subject.

According to another aspect of the present disclosure, a system for medical imaging may be provided. The system may include one or more storage devices and one or more processors configured to communicate with the one or more storage devices. The one or more storage devices may a set of instructions. When the one or more processors execute the set of instructions, the one or more processors may be directed to cause the system to perform one or more of the following operations. The system may automatically determine that a positioning procedure of a subject has been finished based on image data of the subject captured by an image capturing device. The system may also obtain status information of a medical device. The system may further cause the medical device to perform a scan on the subject based on a determination result that the positioning procedure of the subject has been finished, the status information of the medical device, and a starting signal of the scan.

According to yet another aspect of the present disclosure, a method for medical imaging may be provided. The method may include determining one or more preset values of one or more acquisition parameters of a medical device based on a region of a subject to be scanned. The method may also include determining morphological information of the subject based on image data of the subject captured by an image capturing device. The method may also include determining one or more values of the one or more acquisition parameters of the medical device based on the one or more preset values of the one or more acquisition parameters and the morphological information of the subject. The method may further include causing the medical device to perform a scan on the subject based on the one or more values of the one or more acquisition parameters.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Figure 2:
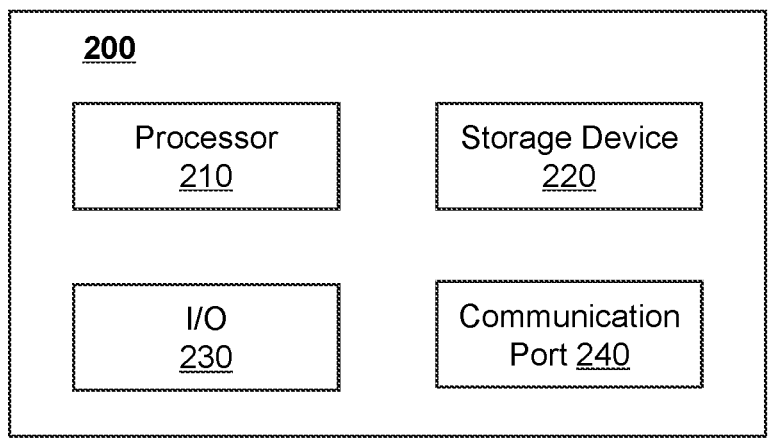
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a threedimensional (3D) image, a four-dimensional (4D), etc. The term "pixel" and "voxel" in the present disclosure are used interchangeably to refer to an element of an image. The term "region," "location," and "area" in the present disclosure may refer to a location of an anatomical structure shown in the image or an actual location of the anatomical structure existing in or on a subject's body, since the image may indicate the actual location of a certain anatomical structure existing in or on the subject's body. The term "an image of a subject" may be referred to as the subject for brevity. Segmentation of an image of a subject may be referred to as segmentation of the subject.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

A conventional medical scan procedure often involves a lot of human intervention. For example, a user (e.g., a doctor, an operator, a technician, etc.) needs to guide a subject to perform a positioning procedure based on experiences or a reference position until the position and the pose of the subject meet the requirements of a scan, and then the user needs to control a medical device to perform the scan on the subject according to one or more preset values of one or more acquisition parameters. If the scan performed using the preset value(s) of the acquisition parameter(s) cannot meet the requirements of a user (e.g., a doctor), for example, one or more images collected by the scan have a low image quality and do not meet diagnosis requirements of the user, the user may need to manually adjust the preset value(s) of the one or more acquisition parameters according to experiences. Hence, the conventional medical scan procedure may have a limited efficiency and accuracy. Thus, it may be desirable to develop systems and methods for automated medical imaging. As used herein, the terms "automatic" and "automated" are used interchangeable referring to methods and systems that analyze information and generates results with little or no direct human intervention.

An aspect of the present disclosure relates to systems and methods for controlling a medical device. The systems may automatically determine that a positioning procedure of a subject has been finished based on image data of the subject captured by an image capturing device. The systems may also obtain status information of the medical device. The systems may also determine one or more values of one or more acquisition parameters of the medical device. The systems may further cause the medical device to perform a scan on the subject based on a determination result that the positioning procedure of the subject has been finished, the status information of the medical device, a starting signal of the scan, and the one or more values of the one or more acquisition parameters of the medical device. Compared with the conventional medical scan procedure which involves a lot of human intervention, the systems and methods of the present disclosure may be implemented with reduced or minimal or without user intervention, which is more efficient and accurate by, e.g., reducing the workload of a user.

In addition, in some embodiments, one or more values of one or more acquisition parameters of the medical device may be determined based on one or more preset values of the one or more acquisition parameters and morphological information of the subject, which are more accurate for considering the actual feature of the subject.

Moreover, in some embodiments, the systems and methods of the present disclosure may be implemented using an Artificial Intelligence (AI) technology (e.g., an image recognition technology). For example, the systems and methods of the present disclosure may be implemented based on one or more machine learning models (e.g., a morphological information determination model, an acquisition parameter determination model). The utilization of the machine learning model(s) may further improve the accuracy and/or efficiency of the medical imaging.

Figure 1:
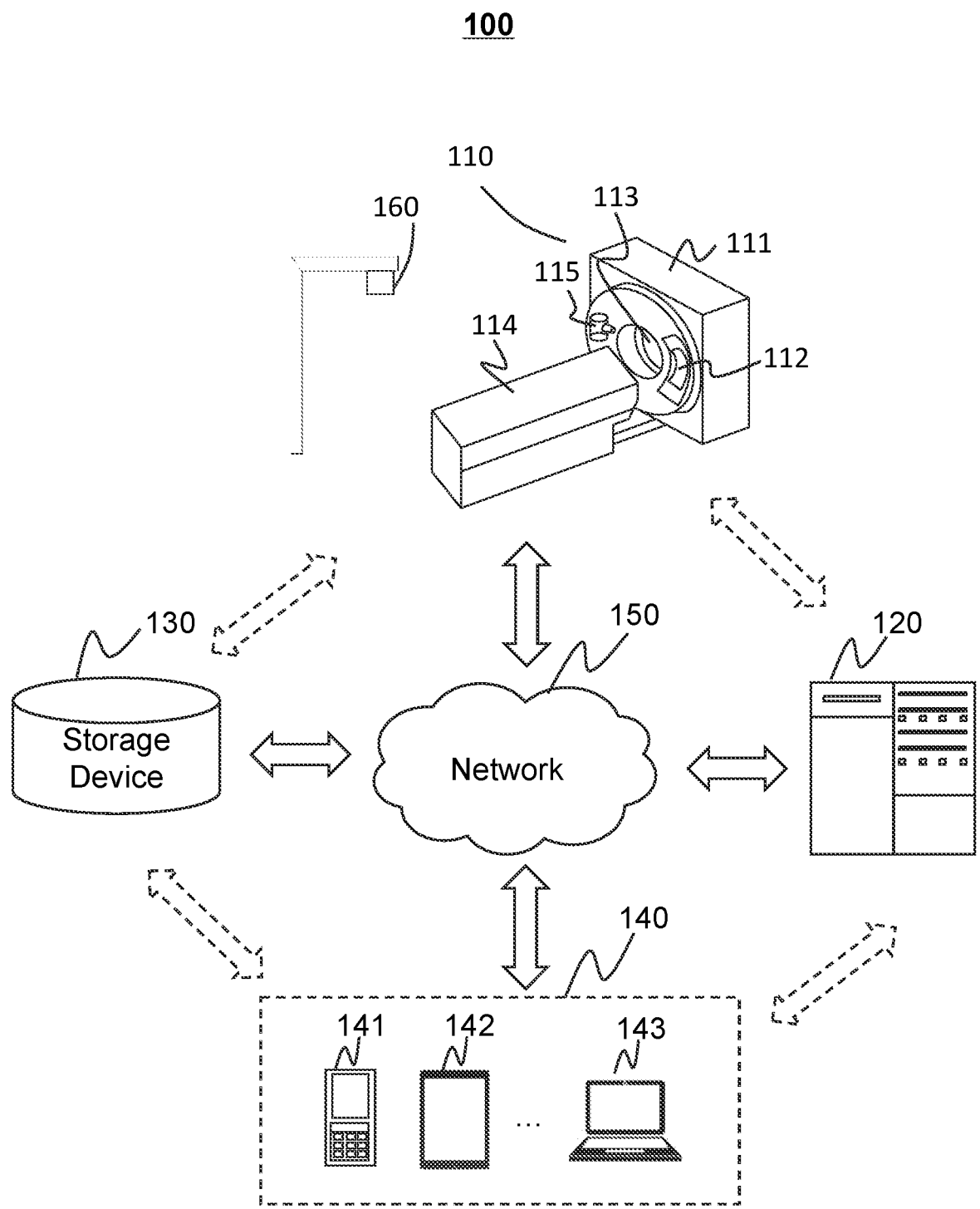
FIG. 1 is a schematic diagram illustrating an exemplary medical system according to some embodiments of the present disclosure.

FIG. 1 is a schematic diagram illustrating an exemplary medical system 100 according to some embodiments of the present disclosure. As shown, the medical system 100 may include a medical device 110, a processing device 120, a storage device 130, one or more terminals 140, a network 150, and an image capturing device 160. In some embodiments, the medical device 110, the processing device 120, the storage device 130, the terminal(s) 140, and/or the image capturing device 160 may be connected to and/or communicate with each other via a wireless connection, a wired connection, or a combination thereof. The connection between the components of the medical system 100 may be variable. Merely by way of example, the medical device 110 may be connected to the processing device 120 through the network 150 or directly. As a further example, the storage device 130 may be connected to the processing device 120 through the network 150 or directly.

The medical device 110 may be configured to scan and/or treat a subject. Merely by way of example, the medical device 110 may generate or provide image data related to a subject via scanning the subject. For illustration purposes, image data of a subject acquired using the medical device 110 is referred to as medical image data, and image data of the subject acquired using the image capturing device 160 is referred to as image data. In some embodiments, the subject may include a biological subject and/or a non-biological subject. For example, the subject may include a specific portion of a body, such as the head, the thorax, the abdomen, or the like, or a combination thereof. As another example, the subject may be a man-made composition of organic and/or inorganic matters that are with or without life. In some embodiments, the medical system 100 may include modules and/or components for performing imaging and/or related analysis. In some embodiments, the medical image data relating to the subject may include projection data, one or more images of the subject, etc. The projection data may include raw data generated by the medical device 110 by scanning the subject and/or data generated by a forward projection on an image of the subject.

In some embodiments, the medical device 110 may be a non-invasive biomedical medical imaging device for disease diagnostic or research purposes. The medical device 110 may include a single modality scanner and/or a multi-modality scanner. The single modality scanner may include, for example, an ultrasound scanner, an X-ray scanner, an computed tomography (CT) scanner, a magnetic resonance imaging (MRI) scanner, an ultrasonography scanner, a positron emission tomography (PET) scanner, an optical coherence tomography (OCT) scanner, an ultrasound (US) scanner, an intravascular ultrasound (IVUS) scanner, a near infrared spectroscopy (NIRS) scanner, a far infrared (FIR) scanner, or the like, or any combination thereof. The multi-modality scanner may include, for example, an X-ray imaging-magnetic resonance imaging (X-ray-MRI) scanner, a positron emission tomography-X-ray imaging (PET-X-ray) scanner, a single photon emission computed tomography-magnetic resonance imaging (SPECT-MRI) scanner, a positron emission tomography-computed tomography (PET-CT) scanner, a digital subtraction angiography-magnetic resonance imaging (DSA-MRI) scanner, etc. It should be noted that the scanner described above is merely provided for illustration purposes, and not intended to limit the scope of the present disclosure. The term "imaging modality" or "modality" as used herein broadly refers to an imaging method or technology that gathers, generates, processes, and/or analyzes imaging information of a subject.

In some embodiments, the medical device 110 may include a gantry 111, a detector 112, a detection region 113, a scanning table 114, and a radiation source 115. The gantry 111 may support the detector 112 and the radiation source 115. The subject may be placed on the scanning table 114 and moved into the detection region 113 to be scanned. The radiation source 115 may emit radioactive rays to the subject. The radioactive rays may include a particle ray, a photon ray, or the like, or a combination thereof. In some embodiments, the radioactive rays may include a plurality of radiation particles (e.g., neutrons, protons, electron, µ-mesons, heavy ions), a plurality of radiation photons (e.g., X-ray, γ-ray, ultraviolet, laser), or the like, or a combination thereof. The detector 112 may detect radiation and/or a radiation event (e.g., gamma photons) emitted from the detection region 113. In some embodiments, the detector 112 may include a plurality of detector units. The detector units may include a scintillation detector (e.g., a cesium iodide detector) or a gas detector. The detector unit may be a single-row detector or a multi-rows detector.

In some embodiments, the medical device 110 may be or include an X-ray imaging device, for example, a computed tomography (CT) scanner, a digital radiography (DR) scanner (e.g., a mobile digital radiography), a digital subtraction angiography (DSA) scanner, a dynamic spatial reconstruction (DSR) scanner, an X-ray microscopy scanner, a multi-modality scanner, etc. For example, the X-ray imaging device may include a support, an X-ray source, and a detector. The support may be configured to support the X-ray source and/or the detector. The X-ray source may be configured to emit X-rays toward the subject to be scanned. The detector may be configured to detect X-rays passing through the subject. In some embodiments, the X-ray imaging device may be, for example, a C-shape X-ray imaging device, an upright X-ray imaging device, a suspended X-ray imaging device, or the like.

In some embodiments, the medical device 110 may include a radiotherapy (RT) device, such as a conformal radiation therapy device, an image-guided radiation therapy (IGRT) device, an intensity-modulated radiation therapy (IMRT) device, an intensity-modulated arc therapy (IMAT) device, an emission guided radiation therapy (EGRT), or the like. The RT device may be configured to deliver a radiotherapy treatment to a subject. For example, the treatment device may deliver one or more radiation beams to a treatment region (e.g., a tumor) of a subject for causing an alleviation of the subject's symptom. A radiation beam may include a plurality of radiation beamlets.

The processing device 120 may process data and/or information obtained from the medical device 110, the storage device 130, the terminal(s) 140, and/or the image capturing device 160. For example, the processing device 120 may automatically determine that a positioning procedure of a subject has been finished based on image data of the subject captured by the image capturing device 160. As another example, the processing device 120 may obtain status information of the medical device 110. As still another example, the processing device 120 may cause the medical device 110 to perform a scan on the subject based on a determination result that the positioning procedure of the subject has been finished, the status information of the medical device 110, and a starting signal of the scan.

In some embodiments, the processing device 120 may be a single server or a server group. The server group may be centralized or distributed. For example, the processing device 120 may generate one or more trained models that can be used in medical imaging and/or treatment. As another example, the processing device 120 may apply the trained model(s) in medical imaging and/or treatment. In some embodiments, the trained model(s) may be generated by a processing device, while the application of the trained model(s) may be performed on a different processing device. In some embodiments, the trained model(s) may be generated by a processing device of a system different from the medical system 100 or a server different from the processing device 120 on which the application of the trained model(s) is performed. For instance, the trained model(s) may be generated by a first system of a vendor who provides and/or maintains such trained model(s), while the medical imaging may be performed on a second system of a client of the vendor. In some embodiments, the application of the trained model(s) may be performed online in response to a request for medical imaging. In some embodiments, the trained model(s) may be generated offline.

In some embodiments, the trained model(s) may be generated and/or updated (or maintained) by, e.g., the manufacturer of the medical device 110 or a vendor. For instance, the manufacturer or the vendor may load the trained model(s) into the medical system 100 or a portion thereof (e.g., the processing device 120) before or during the installation of the medical device 110 and/or the processing device 120, and maintain or update the trained model(s) from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 150. The program may include a new model or a portion of a model that substitutes or supplements a corresponding portion of the model.

In some embodiments, the processing device 120 may be local to or remote from the medical system 100. For example, the processing device 120 may access information and/or data from the medical device 110, the storage device 130, the terminal(s) 140, and/or the image capturing device 160 via the network 150. As another example, the processing device 120 may be directly connected to the medical device 110, the terminal(s) 140, the storage device 130, and/or the image capturing device 160 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 200 having one or more components as described in connection with FIG. 2.

In some embodiments, the processing device 120 may include one or more processors (e.g., single-core processor(s) or multi-core processor(s)). Merely by way of example, the processing device 120 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

The storage device 130 may store data, instructions, and/or any other information. In some embodiments, the storage device 130 may store data obtained from the processing device 120, the terminal(s) 140, the medical device 110, and/or the image capturing device 160. For example, the storage device 130 may store image data collected by the image capturing device 160. As another example, the storage device 130 may store personal information of a subject. As still another example, the storage device 130 may store positioning guidance information. In some embodiments, the storage device 130 may store data and/or instructions that the processing device 120 may execute or use to perform exemplary methods described in the present disclosure.

In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components of the medical system 100 (e.g., the processing device 120, the terminal(s) 140). One or more components of the medical system 100 may access the data or instructions stored in the storage device 130 via the network 150. In some embodiments, the storage device 130 may be part of the processing device 120.

The terminal(s) 140 may enable user interaction between a user and the medical system 100. For example, the terminal(s) 140 may display positioning guidance information. In some embodiments, the terminal(s) 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 140 may include an input device, an output device, etc. In some embodiments, the terminal(s) 140 may be part of the processing device 120.

The network 150 may include any suitable network that can facilitate the exchange of information and/or data for the medical system 100. In some embodiments, one or more components of the medical system 100 (e.g., the medical device 110, the processing device 120, the storage device 130, the terminal(s) 140) may communicate information and/or data with one or more other components of the medical system 100 via the network 150. For example, the processing device 120 may obtain medical image data from the medical device 110 via the network 150. As another example, the processing device 120 may obtain user instruction(s) from the terminal(s) 140 via the network 150.

The network 150 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

The image capturing device 160 may be configured to capture image data of the subject before, during, and/or after the medical device 110 performs a scan or a treatment on the subject. For example, before the scan, the image capturing device 160 may capture image data of the subject, which may be used to determine that a positioning procedure of the subject has been finished. As another example, after the subject is positioned at a scan position (i.e., a specific position for receiving the scan), the image capturing device 160 may be configured to capture image data of the subject, which may be used to check whether the position of the subject needs to be adjusted.

The image capturing device 160 may be and/or include any suitable device that is capable of capturing image data of the subject. For example, the image capturing device 160 may include a camera (e.g., a digital camera, an analog camera, etc.), a red-green-blue (RGB) sensor, an RGB-depth (RGB-D) sensor, or another device that can capture color image data of the subject. As another example, the image capturing device 160 may be used to acquire point-cloud data of the subject. The point-cloud data may include a plurality of data points, each of which may represent a physical point on a body surface of the subject and can be described using one or more feature values of the physical point (e.g., feature values relating to the position and/or the composition of the physical point). Exemplary image capturing devices 160 capable of acquiring point-cloud data may include a 3D scanner, such as a 3D laser imaging device, a structured light scanner (e.g., a structured light laser scanner). Merely by way of example, a structured light scanner may be used to execute a scan on the subject to acquire the point cloud data. During the scan, the structured light scanner may project structured light (e.g., a structured light spot, a structured light grid) that has a certain pattern toward the subject. The point-cloud data may be acquired according to the structure light projected on the subject. As yet another example, the image capturing device 160 may be used to acquire depth image data of the subject. The depth image data may refer to image data that includes depth information of each physical point on the body surface of the subject, such as a distance from each physical point to a specific point (e.g., an optical center of the image capturing device 160). The depth image data may be captured by a range sensing device, e.g., a structured light scanner, a time-of-flight (TOF) device, a stereo triangulation camera, a sheet of light triangulation device, an interferometry device, a coded aperture device, a stereo matching device, or the like, or any combination thereof.

In some embodiments, the image capturing device 160 may be a device independent from the medical device 110 as shown in FIG. 1. For example, the image capturing device 160 may be a camera mounted on the ceiling in an examination room where the medical device 110 is located or out of the examination room. Alternatively, the image capturing device 160 may be integrated into or mounted on the medical device 110 (e.g., the gantry 111). In some embodiments, the image data acquired by the image capturing device 160 may be transmitted to the processing device 120 for further analysis. Additionally or alternatively, the image data acquired by the image capturing device 160 may be transmitted to a terminal device (e.g., the terminal(s) 140) for display and/or a storage device (e.g., the storage device 130) for storage.

In some embodiments, the image capturing device 160 may be configured to capture image data of the subject continuously or intermittently (e.g., periodically) before, during, and/or after a scan or a treatment of the subject performed by the medical device 110. In some embodiments, the acquisition of the image data by the image capturing device 160, the transmission of the captured image data to the processing device 120, and the analysis of the image data may be performed substantially in real time so that the image data may provide information indicating a substantially real-time status of the subject.

In some embodiments, a medical imaging procedure disclosed in the present application may include a plurality of operations. Different operations may be performed based on a same set of image data or different sets of image data of the subject captured by one or more image capturing devices 160. For example, the determination of that a positioning procedure of the subject has been finished as described in operation 510, the determination of positioning guidance information as described in operation 615, the determination of a posture of the subject as described in operation 620, the determination of morphological information of the subject as described in operation 720 may be performed based on a same set of image data or different sets of image data of the subject captured. The different sets of image data of the subject may be captured by different image capturing devices 160 or a same image capturing device 160 at different times. For the convenience of descriptions, the term "image data of the subject" used in detail descriptions regarding the operations (e.g., FIGS. 5-7) refers to a same set of image data or different sets of image data of the subject unless the context clearly indicates otherwise.

It should be noted that the above description of the medical system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the medical system 100 may include one or more additional components. Additionally or alternatively, one or more components of the medical system 100, such as the image capturing device 160 or the medical device 110 described above may be omitted. As another example, two or more components of the medical system 100 may be integrated into a single component. Merely by way of example, the processing device 120 (or a portion thereof) may be integrated into the medical device 110 or the image capturing device 160.

FIG. 2 is a schematic diagram illustrating exemplary hardware and/or software components of a computing device 200 according to some embodiments of the present disclosure. The computing device 200 may be used to implement any component of the medical system 100 as described herein. For example, the processing device 120 and/or the terminal 140 may be implemented on the computing device 200, respectively, via its hardware, software program, firmware, or a combination thereof. Although only one such computing device is shown, for convenience, the computer functions relating to the medical system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 120 in accordance with techniques described herein. The computer instructions may include, for example, routines, programs, subjects, components, data structures, procedures, modules, and functions, which perform particular functions described herein. For example, the processor 210 may process image data obtained from the medical device 110, the terminal(s) 140, the storage device 130, the image capturing device 160, and/or any other component of the medical system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the medical device 110, the terminal(s) 140, the storage device 130, the image capturing device 160, and/or any other component of the medical system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure. For example, the storage device 220 may store a program for the processing device 120 to execute to cause a medical device to perform a scan on a subject based on a determination result that a positioning procedure of the subject has been finished, status information of the medical device, and a starting signal of the scan.

The I/O 230 may input and/or output signals, data, information, etc. In some embodiments, the I/O 230 may enable a user interaction with the processing device 120. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 150) to facilitate data communications. The communication port 240 may establish connections between the processing device 120 and the medical device 110, the terminal(s) 140, the image capturing device 160, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
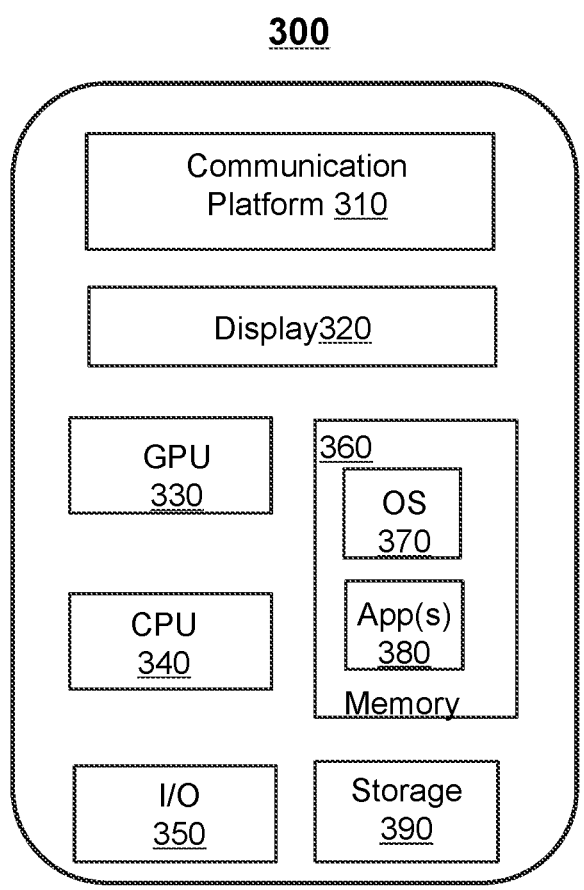
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. In some embodiments, one or more components (e.g., a terminal 140 and/or the processing device 120) of the medical system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the medical system 100. User interactions with the information stream may be achieved via the I/O 350 and provided to the processing device 120 and/or other components of the medical system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
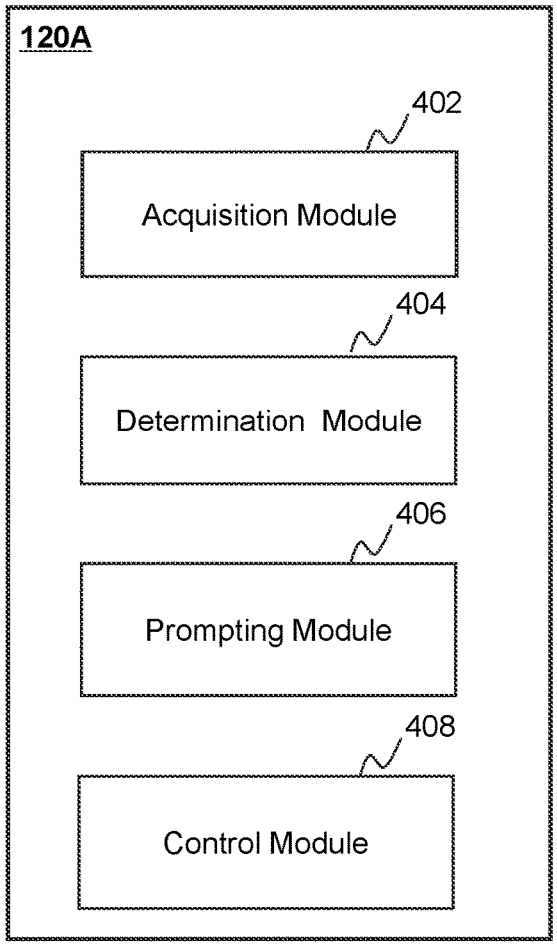
FIGS. 4A and 4B are block diagrams illustrating exemplary processing devices according to some embodiments of the present disclosure.
Figure 4B:
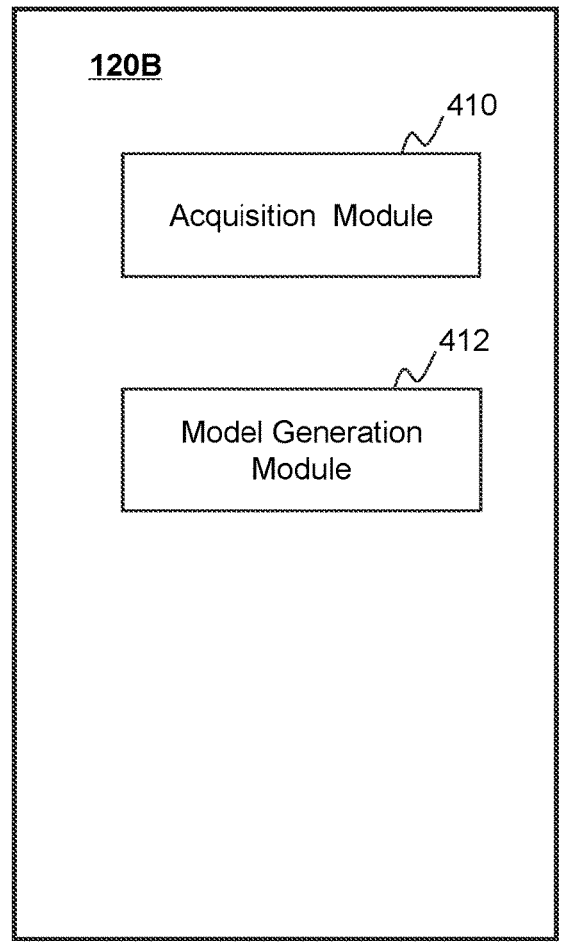

FIGS. 4A and 4B are block diagrams illustrating exemplary processing devices 120A and 120B according to some embodiments of the present disclosure. The processing devices 120A and 120B may be exemplary processing devices 120 as described in connection with FIG. 1. In some embodiments, the processing device 120A may be configured to implement methods for medical imaging disclosed herein. The processing device 120B may be configured to generate the one or more machine learning models. In some embodiments, the machine learning model(s) generated by the processing device 120B may be used by the processing device 120A during the implementation of the methods for medical imaging.

In some embodiments, the processing devices 120A and 120B may be respectively implemented on a processing unit (e.g., a processor 210 illustrated in FIG. 2 or a CPU 340 as illustrated in FIG. 3). Merely by way of example, the processing devices 120A may be implemented on a CPU 340 of a terminal device, and the processing device 120B may be implemented on a computing device 200. Alternatively, the processing devices 120A and 120B may be implemented on a same computing device 200 or a same CPU 340. For example, the processing devices 120A and 120B may be implemented on a same computing device 200.

As shown in FIG. 4A, the processing device 120A may include an acquisition module 402, a determination module 404, a prompting module 406, and a control module 408.

The acquisition module 402 may be configured to obtain information relating to the medical system 100. For example, the acquisition module 402 may obtain status information of a medical device. The status information of the medical device may indicate whether one or more components of the medical device are in a ready state to perform the scan. As another example, the acquisition module 402 may obtain personal information of a subject. For example, the personal information of the subject may include information relating to a region to be scanned, height information, weight information, identity information, or the like, or any combination thereof, of the subject. As still another example, the acquisition module 402 may obtain a posture of the subject. The posture of the subject may indicate a current position and/or a current pose of the subject. More descriptions regarding the obtaining of the status information of the medical device, the personal information and the posture of the subject may be found elsewhere in the present disclosure. See, e.g., operations 520, 610, and 620, and relevant descriptions thereof.

The determination module 404 may be configured to automatically determine that a positioning procedure of the subject has been finished based on image data of the subject captured by an image capturing device. More descriptions regarding the determination of that a positioning procedure of the subject has been finished may be found elsewhere in the present disclosure. See, e.g., operation 510 in FIG. 5 and relevant descriptions thereof.

In some embodiments, the determination module 404 may be configured to determine one or more values of one or more acquisition parameters of the medical device. An acquisition parameter of the medical device refers to a parameter according to which the scan of the subject is performed. Exemplary acquisition parameters of the medical device may include a position and/or one or more motion parameters (e.g., a rotation speed, a moving distance, etc.) of a component of the medical device (e.g., a gantry, a scanning table, a detector), a size and a shape of a light field of a beam limiting device of the medical device, one or more exposure parameters of a high-voltage generator, a scan time, or the like, or any combination thereof. More descriptions regarding determination of the one or more values of the one or more acquisition parameters may be found elsewhere in the present disclosure. See, e.g., operation 530 in FIG. 5 and relevant descriptions thereof.

The prompting module 406 may be configured to prompt the subject to send a starting signal of the scan based on the determination result that the positioning procedure of the subject has been finished. As used herein, a starting signal of the scan may indicate that the scan can be started. More descriptions regarding prompting the subject to send a starting signal of the scan may be found elsewhere in the present disclosure. See, e.g., operation 645 in FIG. 6 and relevant descriptions thereof.

The control module 408 may be configured to cause the medical device to perform the scan on the subject based on a determination result that the positioning procedure of the subject has been finished, the status information of the medical device, a starting signal of the scan, and the one or more values of the one or more acquisition parameters of the medical device. More descriptions regarding causing the medical device to perform the scan on the subject may be found elsewhere in the present disclosure. See, e.g., operation 540 in FIG. 5 and relevant descriptions thereof.

As shown in FIG. 4B, the processing device 120B may include an acquisition module 410 and a model generation module 412.

The acquisition module 410 may be configured to obtain training data used to generate a machine learning model, such as a morphological information determination model, acquisition parameter determination model, or the like, or any combination thereof. For example, the acquisition module 410 may be configured to obtain one or more training samples and a preliminary model for generating the morphological information determination model. More descriptions regarding the acquisition of the training sample(s) and the preliminary model may be found elsewhere in the present disclosure. See, e.g., operation 720 in FIG. 7 and relevant descriptions thereof.

The model generation module 412 may be configured to generate one or more machine learning models by model training. For example, the model generation module 412 may be configured to generate the morphological information determination model by training the preliminary model using the one or more training samples. More descriptions regarding the generation of the morphological information determination model may be found elsewhere in the present disclosure. See, e.g., operation 720 in FIG. 7 and relevant descriptions thereof.

In some embodiments, the one or more machine learning models may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the one or more machine learning models may be a supervised learning algorithm, a semi-supervised learning algorithm, an unsupervised learning algorithm, or the like.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120A and/or the processing device 120B may share two or more of the modules, and any one of the modules may be divided into two or more units. For instance, the processing devices 120A and 120B may share a same acquisition module; that is, the acquisition module 402 and the acquisition module 410 are a same module. In some embodiments, the processing device 120A and/or the processing device 120B may include one or more additional modules, such as a storage module (not shown) for storing data. In some embodiments, the processing device 120A and the processing device 120B may be integrated into one processing device 120.

Figure 5:
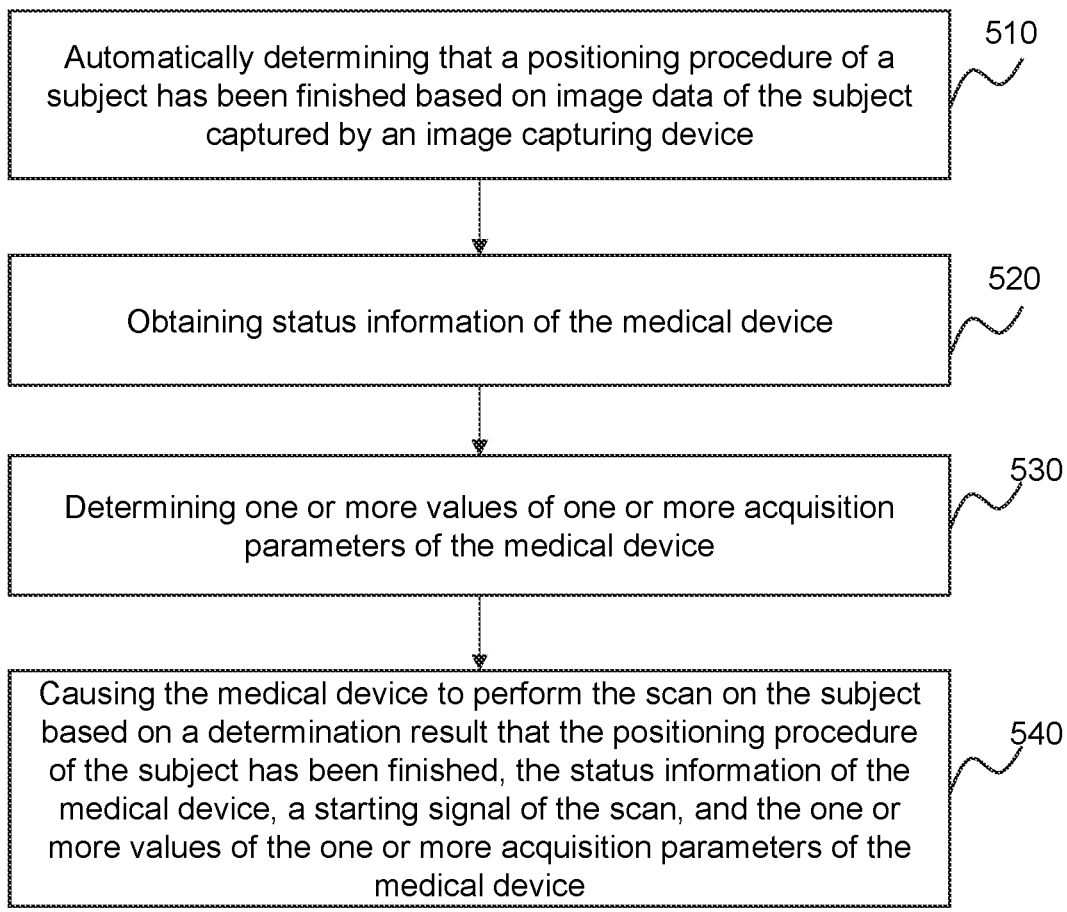
FIG. 5 is a flowchart illustrating an exemplary process for medical imaging according to some embodiments of the present disclosure.

FIG. 5 is a flowchart illustrating an exemplary process for medical imaging according to some embodiments of the present disclosure. In some embodiments, process 500 may be executed by the medical system 100. For example, the process 500 may be implemented as a set of instructions (e.g., an application) stored in a storage device (e.g., the storage device 130, the storage device 220, and/or the storage 390). In some embodiments, the processing device 120A (e.g., the processor 210 of the computing device 200, the CPU 340 of the mobile device 300, and/or one or more modules illustrated in FIG. 4A) may execute the set of instructions and accordingly be directed to perform the process 500.

In some embodiments, the process 500 may be implemented to control a medical device to perform a scan on a subject. As used herein, the subject may include a biological subject and/or a non-biological subject (or a portion thereof). For example, the subject may be a human being, an animal, or a portion thereof. As another example, the subject may be a phantom that simulates a human. In some embodiments, the subject may be a patient (or a portion thereof).

The medical device may include a medical imaging device. Exemplary medical imaging devices may include an X-ray imaging device (e.g., a suspended X-ray imaging device, a C-arm X-ray imaging device), a digital radiography (DR) device (e.g., a mobile digital X-ray imaging device), a CT device, a PET device, an MRI device, or the like, as described elsewhere in the present disclosure. Merely by way of example, the medical device may be an X-ray imaging device including a scanning table (e.g., the scanning table 114), a detector (e.g., the detector 112), an X-ray source (e.g., the radiation source 115), a supporting device, or the like. In some embodiments, the medical device may be a treatment device including an imaging component, and the imaging component of the treatment device may be used to perform the scan on the subject.

In 510, the processing device 120A (e.g., the determination module 404) may automatically determine that a positioning procedure of the subject has been finished based on image data of the subject captured by an image capturing device.

In some embodiments, the image data may include a 2D image, a 3D image, a 4D image (e.g., a time series of 3D images), and/or any related image data (e.g., scan data, projection data) of the subject. The image data may include color image data, point-cloud data, depth image data, mesh data, or the like, or any combination thereof, of the subject.

In some embodiments, the image data of the subject may be captured by an image capturing device, such as the image capturing device 160 mounted in an examination room. The image capturing device may include any type of device that is capable of acquiring image data, such as a 3D camera, an RGB sensor, an RGB-D sensor, a 3D scanner, a 3D laser imaging device, a structured light scanner. In some embodiments, the image capturing device may obtain the image data of the subject when the subject is positioned at a position of a scanning table (e.g., the scanning table 114). In some embodiments, the processing device 120A may obtain the image data of the subject using one or more image capturing devices (e.g., one or more 3D cameras) at different positions (e.g., in front of, behind, a side of the subject, etc.).

As used herein, the positioning procedure of the subject refers to a process to enable the subject to be positioned at a suitable position and/or hold a suitable pose for receiving a scan. In some embodiments, the processing device 120A may obtain personal information and a posture of the subject. The processing device 120A may automatically determine whether the positioning procedure of the subject has been finished based on the personal information and the posture of the subject. More descriptions for the determination of whether the positioning procedure of the subject has been finished may be found elsewhere in the present disclosure. See, e.g., operations 610, 620, and 630 in FIG. 6 and relevant descriptions thereof.

In 520, the processing device 120A (e.g., the acquisition module 402) may obtain status information of the medical device.

The status information of the medical device may indicate whether one or more components of the medical device are in a ready state to perform the scan. For example, the status information of the medical device may include status information of the component(s) of the medical device (e.g., an anode rotation speed of a tube, etc.), high voltage status information, position information of the component(s) of the medical device, relative position information between multiple components of the medical device (e.g., the tube and a detector), or the like, or any combination thereof.

In some embodiments, the status information of the medical device may be automatically obtained by the processing device 120A. Alternatively, the status information of the medical device may be determined manually by a user (e.g., a doctor, an imaging specialist, a technician, etc.).

In 530, the processing device 120A (e.g., the determination module 404) may determine one or more values of one or more acquisition parameters of the medical device.

An acquisition parameter of the medical device refers to a parameter according to which the scan of the subject is performed. Exemplary acquisition parameters of the medical device may include a position and/or one or more motion parameters (e.g., a rotation speed, a moving distance, etc.) of a component of the medical device (e.g., a gantry, a scanning table, a detector), a size and a shape of a light field of a beam limiting device of the medical device, one or more exposure parameters of a high-voltage generator, a scan time, or the like, or any combination thereof.

In some embodiments, the value of an acquisition parameter may be a preset value of the acquisition parameter. In some embodiments, the value of an acquisition parameter may be determined by performing process 700 as described in connection with FIG. 7. For example, the processing device 120A may determine the value(s) of the acquisition parameter(s) of the medical device based on morphological information of the subject. More descriptions for the determination of the value(s) of the acquisition parameter(s) may be found elsewhere in the present disclosure. See, e.g., operations 710, 720, and 730 in FIG. 7 and relevant descriptions thereof. In some embodiments, the values of different acquisition parameters may be determined by different manners.

In 540, the processing device 120A (e.g., the control module 408) may cause the medical device to perform the scan on the subject based on a determination result that the positioning procedure of the subject has been finished, the status information of the medical device, a starting signal of the scan, and the one or more values of the one or more acquisition parameters of the medical device.

As used herein, a starting signal of the scan may indicate that the scan can be started. The processing device 120A may direct the medical device to perform the scan on the subject after (e.g., immediately) the starting signal of the scan is received.

In some embodiments, the starting signal of the scan may include a starting signal sent by the subject, and the processing device 120A may cause the medical device to perform the scan on the subject based on the determination result that the positioning procedure of the subject has been finished, the status information of the medical device, and the starting signal of the scan sent by the subject.

In some embodiments, the starting signal of the scan may include a trigger signal automatically generated based on a state of the subject, and the processing device 120A may cause the medical device to perform the scan on the subject based on the determination result that the positioning procedure of the subject has been finished, the status information of the medical device, and the trigger signal automatically generated based on the state of the subject. More descriptions for the implementation of the scan may be found elsewhere in the present disclosure. See, e.g., operations 670 and 680 in FIG. 6 and relevant descriptions thereof.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. For example, the process 500 may include an additional operation to transmit images collected by the scan to a terminal device (e.g., a terminal 140 of a doctor) for display.

Figure 6:
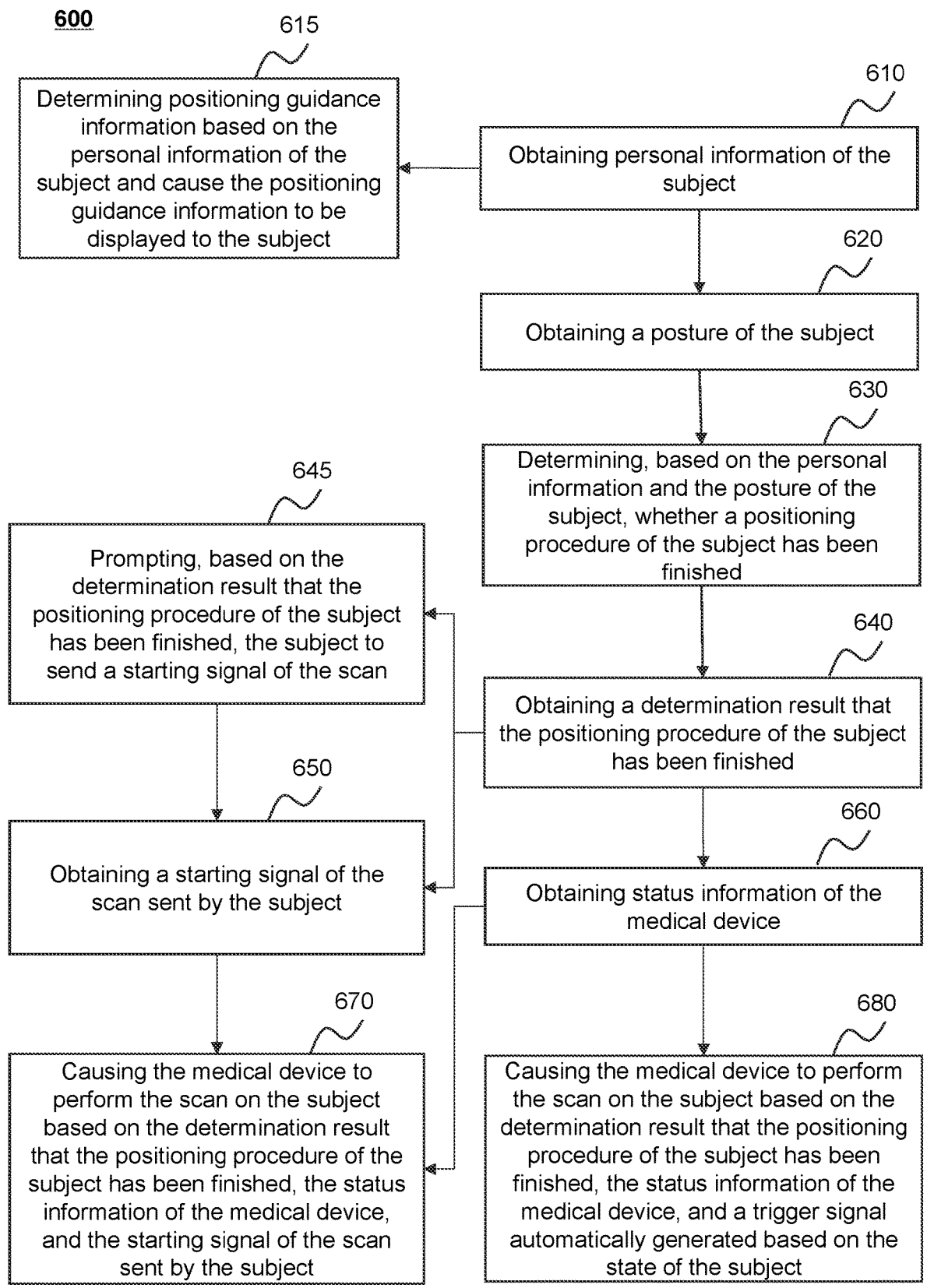
FIG. 6 is a flowchart illustrating an exemplary process for medical imaging according to some embodiments of the present disclosure.

FIG. 6 is a flowchart illustrating an exemplary process for medical imaging according to some embodiments of the present disclosure. In some embodiments, process 600 may be executed by the medical system 100. For example, the process 600 may be implemented as a set of instructions (e.g., an application) stored in a storage device (e.g., the storage device 130, the storage device 220, and/or the storage 390). In some embodiments, the processing device 120A (e.g., the processor 210 of the computing device 200, the CPU 340 of the mobile device 300, and/or one or more modules illustrated in FIG. 4A) may execute the set of instructions and accordingly be directed to perform the process 600.

In some embodiments, the process 600 may be an exemplary embodiment of the process 500 as described in connection with FIG. 5. A medical device may be controlled to perform a scan on a subject.

In 610, the processing device 120A (e.g., the acquisition module 402) may obtain personal information of the subject.

For example, the personal information of the subject may include information relating to a region to be scanned, height information, weight information, identity information, or the like, or any combination thereof, of the subject. In some embodiments, the personal information of the subject may at least include information relating to the region to be scanned. The information relating to the region to be scanned may include an organ or tissue corresponding to the region to be scanned, such as the head, the chest, the heart, the lungs, the abdomen, etc. Additionally or alternatively, the information relating to the region to be scanned may include position information, size information, etc., of the region to be scanned (e.g., a position and a size of a tumor). The identity information of the subject may include a gender, a name, an age, medical history, or the like, or any combination thereof, of the subject.

In some embodiments, the processing device 120A may obtain the personal information of the subject using an Artificial Intelligence (AI) technology (e.g., an image recognition technology). For example, the processing device 120A may obtain an image (e.g., a face image or a body image) of the subject. The image of the subject may be a real-time image captured by an image capturing device mounted in the examination room or a historical image captured by another image capturing device. The processing device 120A may retrieve the personal information of the subject based on the image of the subject from a database (e.g., a hospital database storing patient information). As another example, the processing device 120A may recognize the gender, the age, the height, the weight, etc., of the subject by analyzing the image of the subject.

In some embodiments, the processing device 120A may obtain the personal information of the subject using an identification device (e.g., a card, a bracelet, etc.). For example, the subject may swipe a card on a card reader when entering the examination room. The processing device 120A may retrieve the personal information corresponding to the card from a database based on information collected by the card reader.

In some embodiments, the processing device 120A may perform operation 615 and/or operation 620 after the operation 610 is performed. For example, the processing device 120A may perform operations 615 and 620 simultaneously, that is, the processing device 120A may display positioning guidance information to the subject and obtain a posture of the subject simultaneously.

In 615, the processing device 120A (e.g., the determination module 404) may determine positioning guidance information based on the personal information of the subject and cause the positioning guidance information to be displayed to the subject.

The positioning guidance information may be used to guide the subject to adjust his/her pose and/or position to prepare for the scan.

In some embodiments, the processing device 120A may determine the positioning guidance information based on the region of the subject to be scanned. For example, if the region of the subject to be scanned is the chest, the positioning guidance information may direct the subject to stand upright facing a scanning gantry, align his/her body center with a center line of a cassette of the medical device (e.g., an X-ray cassette), tilt his/her head back slightly, place his/her chin on the upper edge of the cassette, cause the upper edge of the cassette to extend beyond his/her shoulders, cause his/her shoulders to be close to the cassette, cause his/her chest to be close to the cassette, cause his/her arms to hang down naturally, and cause his/her feet to stand apart to stabilize his/her body.

In some embodiments, the processing device 120A may determine the positioning guidance information and cause the positioning guidance information to be displayed to the subject based on the height and/or the weight of the subject. For example, different positioning guidance information for patients having different heights (e.g., different positions at a scanning table to lie) may be previously determined and stored in a storage device. The processing device 120A may determine positioning guidance information corresponding to the height of the subject from the storage device.

In some embodiments, the processing device 120A may determine a real-time position/pose of the subject based on real-time image data of the subject. The processing device may determine the positioning guidance information based on the real-time position/pose of the subject. For example, the positioning guidance information may direct the subject to tilt his/her head to the left, move his/her right leg to the right, etc., based on the real-time pose of the subject. In such cases, the positioning guidance information may be personalized and determined in real-time, which may accurately and efficiently direct the subject to perform the positioning procedure.

In some embodiments, the processing device 120A may cause a terminal device and/or the medical device to display the positioning guidance information to the subject in various forms, such as a voice prompt, a video display, an image display, a text display, etc.

In some embodiments, the processing device 120A may display other guidance information to the subject. Exemplary other guidance information may include information that guides the subject to move to a position to receive the scan after the subject enters the examination room (e.g., direction information that can be displayed via an indicator on the ground), information that guides the subject to drop off objects (e.g., a coat, a jewelry, a mobile phone, etc.) that may interfere with the scan. For example, the processing device 120A may guide the subject to the position to receive the scan according to the region of the subject to be scanned by causing a lighting device (e.g., a LED light) to emit guiding lights. In some embodiments, the positioning guidance information may include guidance information provided by a user (e.g., a doctor).

In some embodiments, the subject may perform a positioning procedure according to the positioning guidance information and/or other guidance information.

In 620, the processing device 120A (e.g., the acquisition module 402) may obtain a posture of the subject.

In some embodiments, the posture of the subject may indicate a current position and/or a current pose of the subject. For example, the posture of the subject may include an orientation of the body, a position of the head, a position of the chest, poses of the arms, poses of the feet, a joint angle of a joint, etc., of the subject. In some embodiments, the posture of the subject may include the position and/or the pose of the region of the subject to be scanned.

In some embodiments, the processing device 120A may obtain the posture of the subject using technologies such as an ultrasonic technology, an infrared technology, a proximity switch technology, etc. For example, the processing device 120A may determine the posture of the subject according to information (e.g., whether there is obstruction, the distance to the subject, etc.) collected by multiple infrared sensors installed at different positions.

In some embodiments, the processing device 120A may determine the posture of the subject based on image data of the subject (e.g., a same set of image data as the image data as described in connection with operation 510 or a different set of image data captured by an image capturing device).

In some embodiments, the processing device 120A may determine the posture of the subject based on the image data of the subject using an AI technology (e.g., an image recognition technology). Merely by of example, the image data of the subject may include a portion corresponding to the subject and a portion corresponding to a scanning table supporting the subject. The processing device 120A may determine one or more first feature points representing the subject and one or more second feature points representing the scanning table from the image data. A first feature point of the subject may be a pixel or voxel in the image data corresponding to a physical point of the subject, and a second feature point of the scanning table may be a pixel or voxel in the image data corresponding to a physical point of the scanning table. The processing device 120A may obtain position information of the scanning table, such as coordinates of one or more physical points of the scanning table in a coordinate system. The processing device 120A may further determine the position of the subject based on the position information of the scanning table, the one or more first feature points of the subject, and the one or more second feature points of the scanning table. Merely by way of example, the processing device 120A may determine a position of the subject in the coordinate system based on the position information of the scanning table and a relative position between the first feature point(s) and the second feature point(s).

In 630, the processing device 120A (e.g., the determination module 404) may automatically determine, based on the personal information and the posture of the subject, whether a positioning procedure of the subject has been finished.

As described in connection with operation 510, the positioning procedure of the subject refers to a process to enable the subject to be positioned at a suitable position and/or hold a suitable pose for receiving a scan.

In some embodiments, the processing device 120A may determine a reference posture of the subject based on the personal information of the subject (e.g., the height, the weight, the age, the region to be scanned, etc., of the subject). The reference posture of the subject refers to a standard posture that the subject needs to hold during the scan. The reference posture may include a reference pose (e.g., a head-first supine pose, a feet-first prone pose, a head-first left lateral recumbent pose, or a feet-first right lateral recumbent pose, or the like) and/or a reference position. For example, if the region of the subject to be scanned is the chest of the subject, the reference posture may be a standard posture for a chest scan, which may be predetermined. As another example, the reference posture may be determined by adjusting the standard posture according to the personal information of the subject. Merely by way of example, it is determined that the subject is obese according to the personal information of the subject, the processing device 120A may determine that the subject needs to be closer to a flat panel detector of the medical device than the standard position of a chest scan.

In some embodiments, the processing device 120A may perform a comparison between the posture and the reference posture of the subject. The processing device 120A may further determine whether the positioning procedure of the subject has been finished based on the comparison between the posture and the reference posture of the subject.

Merely by way of example, the reference posture may include a contour region. The contour region refers to an estimated region occupied by the subject when the subject holds the reference posture. For example, the contour region may include an estimated projection region of the subject when he/she holds the reference posture on a scanning table in a projection direction (e.g., a direction perpendicular to the scanning table of the medical device). The processing device 120A may determine a projected area of the subject in the projection direction and an overlap area between the projected area and the contour region. The processing device 120A may further determine whether the positioning procedure of the subject has been finished based on a ratio of the overlapped area to the projected area. For example, if the ratio is greater than a first threshold, the processing device 120A may determine that the positioning procedure of the subject has been finished. The first threshold may be set manually by a user (e.g., an engineer), according to an experience value, or according to a default setting of the medical system 100, or determined by the processing device 120A according to an actual need, such as 90%, 80%, 95%, or a larger or smaller value.

As another example, the processing device 120A may determine a difference between a current position and a reference position of the region to be scanned based on the posture and the reference posture of the subject. Merely by way of example, if the difference between the current position and the reference position of the region to be scanned is smaller than a preset value, the processing device 120A may determine that the positioning procedure of the subject has been finished.

In some embodiments, in response to determining that the positioning procedure of the subject has been finished, the processing device 120A may perform operation 640. In response to determining that the positioning procedure of the subject has not been finished, the processing device 120A may continue to display the positioning guidance information to the subject until the positioning procedure of the subject is finished. Optionally, the processing device 120A may adjust the positioning guidance information based on the posture (e.g., a real-time posture) of the subject, and display the adjusted positioning guidance information to the subject.

In 640, the processing device 120A (e.g., the acquisition module 402) may obtain a determination result that the positioning procedure of the subject has been finished.

In some embodiments, in response to determining that the positioning procedure of the subject has been finished, the processing device 120A may obtain the determination result that the positioning procedure of the subject has been finished. In some embodiments, in response to determining that the positioning procedure of the subject has been finished and the posture of the subject remains unchanged for more than a certain time (e.g., 2 seconds, 3 seconds, 5 seconds, etc.), the processing device 120A may obtain the determination result that the positioning procedure of the subject has been finished to prevent a situation that the subject moves.

In some embodiments, the processing device 120A may perform operation 645, operation 650, and/or operation 660 after the determination result that the positioning procedure of the subject has been finished is obtained. In some embodiments, operation 640 and/or operation 650 may be omitted. In some embodiments, operations 650 and 660 may be performed simultaneously or sequentially.

In 645, the processing device 120A (e.g., the prompting module 406) may prompt, based on the determination result that the positioning procedure of the subject has been finished, the subject to send a starting signal of the scan.

In some embodiments, the medical device may be controlled by the subject. After the determination result that the positioning procedure of the subject has been finished is obtained, the processing device 120A may prompt the subject that the positioning procedure of the subject has been finished and to send the starting signal of the scan. In some embodiments, the processing device 120A may prompt the subject using, such as sound information, text information, or image information, etc. For example, the processing device 120A may direct a terminal or the medical device to broadcast sound information, such as "the positioning procedure of the subject has been finished," "please send the starting signal of the scan," "please press the scan button," etc., to the subject.

In 650, the processing device 120A (e.g., the acquisition module 402) may obtain a starting signal of the scan sent by the subject.

As described in connection with operation 540, a starting signal of a scan may indicate that the scan can be started. The processing device 120A may direct the medical device to perform the scan on the subject after (e.g., immediately after) receiving the starting signal of the scan.

In some embodiments, after the subject receives the prompt to send the starting signal sent by the processing device 120A, the subject may send the starting signal of the scan. In some embodiments, the subject may send the starting signal of the scan without receiving the prompt sent by the processing device 120A.

In some embodiments, the starting signal of the scan sent by the subject may include a key signal, a voice signal, a posture signal, etc. For example, the voice signal may include an instruction such as "start," "benign," "execute," etc., spoken by the subject. As another example, the posture signal may include a gesture signal, a nodding signal, or the like. As yet another example, the key signal may be generated by pressing a physical key or a virtual key on, such as a scanning table where the subject lies on.

In 660, the processing device 120A (e.g., the acquisition module 402) may obtain status information of the medical device.

Operation 660 may be performed in a similar manner as operation 520, and the descriptions thereof are not repeated here.

In 670, the processing device 120A (e.g., the control module 408) may cause the medical device to perform the scan on the subject based on the determination result that the positioning procedure of the subject has been finished, the status information of the medical device, and the starting signal of the scan sent by the subject.

When the processing device 120A obtains the determination result that the positioning procedure of the subject has been finished and the starting signal of the scan sent by the subject, and determines that the medical device is in a ready state based on the status information of the medical device, the processing device 120A may cause the medical device to perform the scan on the subject.

In some embodiments, the scan may be performed based on one or more values of one or more acquisition parameters of the medical device. Exemplary acquisition parameters of the medical device may include a position and/or one or more motion parameters (e.g., a rotation speed, a moving distance, etc.) of a component of the medical device (e.g., a gantry, a scanning table, a detector), a size and a shape of a light field of a beam limiting device of the medical device, one or more exposure parameters of a high-voltage generator, a scan time, or the like, or any combination thereof.

In some embodiments, the value of an acquisition parameter may be a preset value of the acquisition parameter. In some embodiments, the value of an acquisition parameter may be determined by performing the process 700 as described in connection with FIG. 7. For example, the processing device 120A may determine the value(s) of the acquisition parameter(s) of the medical device based on morphological information of the subject. More descriptions for the determination of the value(s) of the acquisition parameter(s) may be found elsewhere in the present disclosure. See, e.g., operations 710, 720, and 730 in FIG. 7 and relevant descriptions thereof.

In some embodiments, the starting signal may be a trigger signal automatically generated based on a state of the subject. In such cases, operations 645, 650, and 670 may be omitted, and the processing device 120A may proceed to operation 680 after operation 660.

In 680, the processing device 120A (e.g., the control module 408) may cause the medical device to perform the scan on the subject based on the determination result that the positioning procedure of the subject has been finished, the status information of the medical device, and the trigger signal automatically generated based on the state of the subject.

In some embodiments, the state of the subject may include a breathing state, a motion state, etc., of the subject. The breathing state of the subject may relate to a breathing movement of the subject. The motion state of the subject may relate to whether the region of the subject to be scanned moves or a movement (e.g., a moving distance) of the region of the subject to be scanned.

In some embodiments, the processing device 120A may obtain the breathing state and/or motion state of the subject through a camera (e.g., the image capturing device 160 or another image capturing device) and/or a sensor. For example, the processing device 120A may obtain a video stream of the chest and/or abdomen of the subject captured by the camera. The processing device 120A may determine the breathing state of the subject by analyzing the motion of the chest and/or abdomen of the subject based on the video stream. As another example, the processing device 120A may monitor the motion of one or more preset points on straps tied to the chest and/or abdomen of the subject based on the video stream to obtain the breathing state of the subject. As still another example, the processing device 120A may monitor airflow in the oral cavity and/or the nasal cavity of the subject through one or more sensors to obtain the breathing state of the subject. As still another example, the processing device 120A may obtain a video stream of the subject through the camera, and determine the motion state of the subject based on the video stream, for example, by tracking the motion of feature point(s) and/or region(s) of interest of the subject based on the video stream of the subject.

In some embodiments, the trigger signal may be generated automatically based on the motion state of the subject. Merely by way of example, the processing device 120A may obtain motion information of the subject according to the motion state of the subject. The processing device 120A may generate the trigger signal automatically based on the motion information of the subject.

For example, if the processing device 120A detects that the subject maintains a preset static state (e.g., holding the posture when the positioning procedure of the subject is finished) for a first preset time (e.g., 3 seconds, 5 seconds, 7 seconds, etc.), the processing device 120A may generate the trigger signal automatically. As another example, if the processing device 120A detects that the subject maintains a preset motion mode for a second preset time, the processing device 120A may generate the trigger signal automatically.

In some embodiments, when in the preset motion mode, a motion amplitude of the subject is less than a second threshold (e.g., the region of the subject to be scanned is always located in a specific region). The motion amplitude of the subject may be measured by, for example, a displacement of one or more parts of the subject within a unit time (e.g., 1 ms, 5 ms, 50 ms, etc.) The second threshold may be set manually by a user (e.g., an engineer, doctor), or according to a default setting of the medical system 100, or determined by the processing device 120A according to an actual need. For example, the second threshold may be 1 cm/ms, 3 cm/ms, or any other value. In some embodiments, in the preset motion mode, the subject (or a part of the subject) may change from moving to static. For example, the trigger signal may be generated automatically at the moment when the subject changes from moving to static.

The first preset time and the second preset time may be set manually by a user (e.g., an engineer), or according to a default setting of the medical system 100, or determined by the processing device 120A according to an actual need.

In some embodiments, the trigger signal may be generated automatically based on the breathing state of the subject. Merely by way of example, the processing device 120A may obtain breathing information of the subject according to the breathing state of the subject. The processing device 120A may generate the trigger signal automatically based on the breathing information of the subject.

For example, if the processing device 120A detects that a breathing amplitude of the subject is smaller than a third threshold, the processing device 120A may generate the trigger signal automatically. In some embodiments, the breathing amplitude of the subject may be measured by a volume of gas (e.g., 1 ml, 2 ml, etc.) inhaled or exhaled by the subject per unit time (e.g., 1 ms, 2 ms, etc.). Additionally or alternatively, the breathing amplitude of the subject may be measured by a moving distance (e.g., 1 mm, 2 mm, etc.) of the chest and/or a moving distance (e.g., 1 mm, 2 mm, etc.) of the abdomen of the subject per unit time (e.g., 1 ms, 2 ms, etc.). Merely by way of example, when the subject has just taken a breath but has not yet exhaled or has just exhaled but has not yet inhaled, the breathing amplitude of the subject may be smaller than the third threshold.

In some embodiments, the processing device 120A may predict a period of steady breathing of the subject based on the breathing state of the subject. The trigger signal may be generated during the period of steady breathing of the subject. For example, the processing device 120A may obtain the breathing state of the subject through a camera or a sensor as aforementioned. Since the breathing of the subject generally has a certain regularity, the processing device 120A may determine a breathing regularity of the subject based on the breathing state of the subject, and predict the period of steady breathing of the subject based on the breathing regularity of the subject. The period of steady breathing may include a period when the breathing amplitude of the subject is smaller than the third threshold, the subject is in one or more certain respiratory phases (e.g., an end-exhaling phase), etc., such as a period between 0.5 and 0.7 seconds after the subject has just taken a breath. The processing device 120A may generate the trigger signal based on the period of steady breathing of the subject. For example, the processing device 120A may designate a start time of the period of steady breathing of the subject as a start time of the scan.

In some embodiments, the processing device 120A may generate the trigger signal based on the motion state and the breathing state of the subject. For example, if the processing device 120A detects that the subject remains in a preset static mode for a preset time and the breathing amplitude of the subject is smaller than the third threshold, the processing device 120A may generate the trigger signal.

In some embodiments, the processing device 120A may continuously monitor the posture of the subject. If the subject moves and the posture of the subject fails to meet the requirements of the scan, the processing device 120A may guide the subject to perform the positioning procedure again until the positioning procedure of the subject is completed again. In some embodiments, the processing device 120A may display updated positioning guidance information according to a current pose and/or a current position of the subject. For example, the processing device 120A may display positioning guidance information (e.g., moving the arms, rotating the head, etc.) for adjusting the current pose of the subject according to a difference between the current posture of the subject and the reference posture. As another example, the processing device 120A may display positioning guidance information for adjusting the current position of the subject according to a difference between the current position of the subject and the reference position.

In some embodiments, the processing device 120A may directly cause the medical device to perform the scan after the starting signal is received. Alternatively, the processing device 120A may cause the medical device to perform the scan at a certain time after the starting signal is received (e.g., 2 seconds, 3 seconds after the starting signal is received). After the starting signal is received and before the scan is performed, the processing device 120A may send a reminder to the subject (e.g., a countdown reminder, a reminder to remind the subject to keep still).

In some embodiments, after the scan is completed, the processing device 120A may guide the subject to leave the examination room. For example, the processing device 120A may guide the subject to leave the examination room through a prompt such as a voice prompt, a video prompt, a text prompt, a light prompt, etc. In some embodiments, after the scan is completed, the processing device 120A may upload one or more collected images to a designated database. For example, the collected images may be uploaded to a server (e.g., a cloud server), stored in the storage device of the medical system 100, or the like, or any combination thereof.

Conventionally, a user (e.g., a doctor, an operator, a technician, etc.) needs to guide the subject to perform the positioning procedure based on experiences or a reference posture until the posture of the subject meets the requirements of the scan. Additionally, the user needs to control the medical device to perform the scan on the subject. For example, the user has to visually inspect the subject to determine whether the positioning procedure of the subject is finished and/or whether the subject remains in a preset static state for the first preset time, and send a starting signal to the medical device if the positioning procedure of the subject has been finished and/or the subject remains in a preset static state for the first preset time.

According to some embodiments of the present disclosure, the processing device 120A may cause the positioning guidance information to be displayed to the subject and automatically determine whether the positioning procedure of the subject has been finished. The processing device 120A may cause the medical device to perform the scan on the subject based on the determination result that the positioning procedure of the subject has been finished, the status information of the medical device, and a starting signal of the scan (which may be sent by the subject or automatically generated). Compared with the conventional approach which involves a lot of human intervention, the systems and methods disclosed herein may reduce user intervention and is more efficient and accurate by, e.g., reducing the workload of the user, cross-user variations, and the time needed for scan preparation.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. For example, operation 645 may be omitted. In some embodiments, two or more operations may be performed simultaneously. For example, operations 620 and 615 may be performed simultaneously. As another example, operations 640 and 660 may be performed simultaneously. In some embodiments, operations in the process 600 may be performed in a different order. For example, operation 660 may be performed before operation 640.

Figure 7:
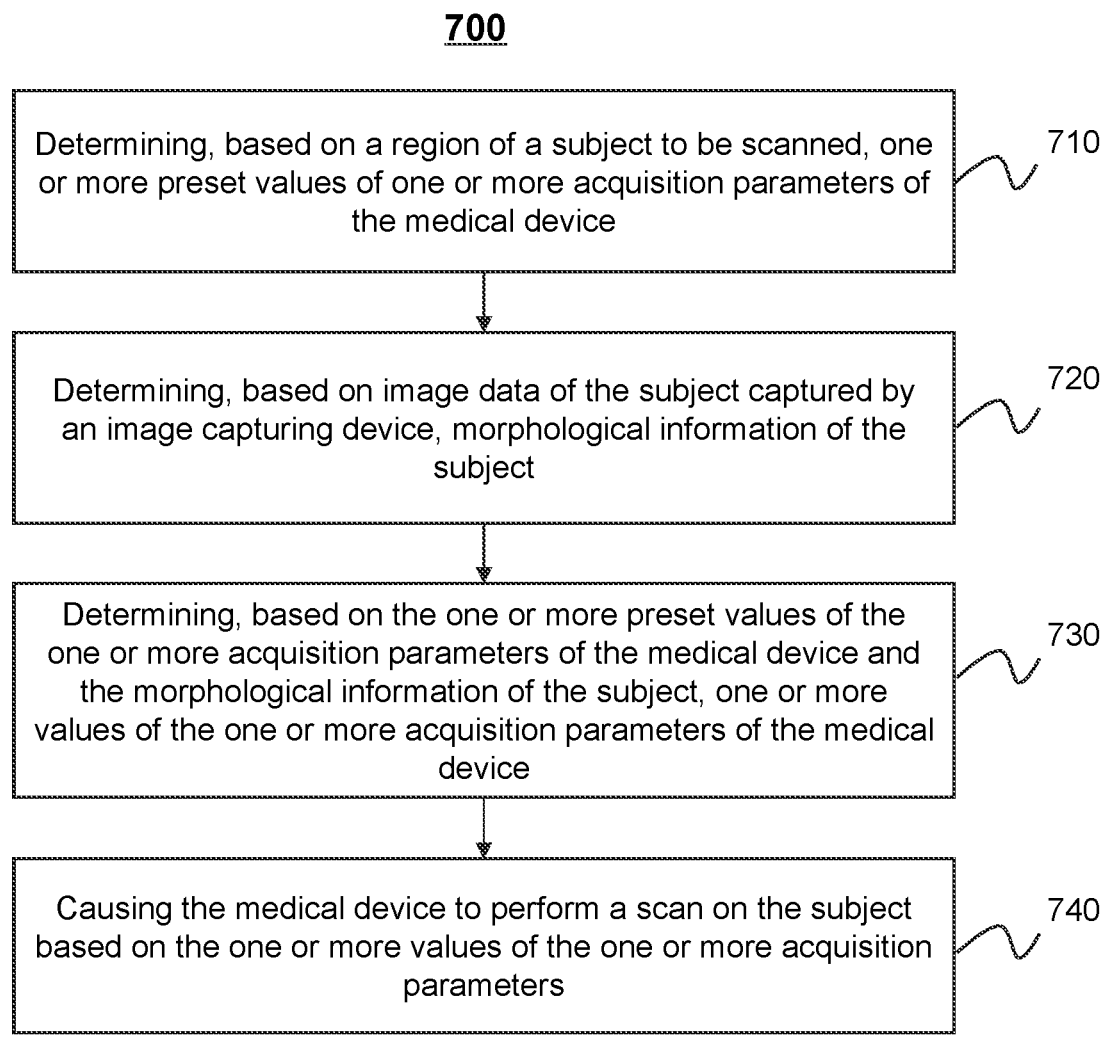
FIG. 7 is a flowchart illustrating an exemplary process for medical imaging according to some embodiments of the present disclosure.

FIG. 7 is a flowchart illustrating an exemplary process for medical imaging according to some embodiments of the present disclosure. In some embodiments, process 700 may be executed by the medical system 100. For example, the process 700 may be implemented as a set of instructions (e.g., an application) stored in a storage device (e.g., the storage device 130, the storage device 220, and/or the storage 390). In some embodiments, the processing device 120A (e.g., the processor 210 of the computing device 200, the CPU 340 of the mobile device 300, and/or one or more modules illustrated in FIG. 4A) may execute the set of instructions and accordingly be directed to perform the process 700.

In some embodiments, one or more operations of the process 700 may be performed to achieve at least part of operation 530 as described in connection with FIG. 5.

In 710, the processing device 120A (e.g., the determination module 404) may determine, based on a region of a subject to be scanned, one or more preset values of one or more acquisition parameters of the medical device.

A region of a subject to be scanned refers to a region of the subject on which a scan is to be performed. For example, the region of the subject to be scanned may include the abdomen, the chest, the brain, the heart, a lung, a region infected by a tumor, or the like, or any combination thereof, of the subject.

In some embodiments, the processing device 120A may obtain the region of the subject to be scanned based on historical or real-time image data of the subject using an AI technology (e.g., an image recognition technology). For example, the processing device 120A may obtain an image (e.g., a face image or a body image) of the subject captured by a camera (e.g., the image capturing device 160 or another image capturing device), and retrieve personal information of the subject from a database. The personal information may include the region of the subject to be scanned. In some embodiments, the processing device 120A may obtain the region of the subject to be scanned using an identification device (e.g., a card, a bracelet, etc.). For example, the subject may swipe a card on a card reader when entering an examination room. The processing device 120A may retrieve the personal information of the subject from a database based on information collected by the card reader. In some embodiments, the region of the subject to be scanned may be input by a user (e.g., a doctor) via a terminal. In some embodiments, the processing device 120A may determine the region of the subject to be scanned by identifying a region of interest (e.g., a lesion region) from the historical or real-time image data of the subject.

Exemplary acquisition parameters of the medical device may include a position and/or one or more motion parameters (e.g., a rotation speed, a moving distance, etc.) of a component of the medical device (e.g., a gantry, a scanning table, a detector), a size and a shape of a light field of a beam limiting device of the medical device, one or more exposure parameters of a high-voltage generator, a scan time, or the like, or any combination thereof. In some embodiments, one or more components of the medical device (e.g., the gantry, the scanning table, and the detector) may be movable. The size of the light field of the beam limiting device may reflect an opening size of the beam limiting device, which may be associated with a scan region of the medical device. Exemplary exposure parameters of the high-voltage generator may include a tube voltage, a tube current, a pulse effective time, or the like, or any combination thereof.

In some embodiments, the scan of the subject may be a stitching scan, and the one or more acquisition parameters of the medical device may include a stitching scan protocol relating to the stitching scan. As used herein, the stitching scan may be implemented by sequentially performing a plurality of scans on different parts of the subject. Each scan may be used to generate a medical image of one of the parts of the subject. The medical images of the parts of the subject may be stitched to generate a stitched image corresponding to a combination of the different parts of the subject. The stitching scan protocol may include a count of the scans, a starting position and an ending position of a movable component (e.g., a scanning table, a radiation source, a detector) of the medical device during the stitching scan, a scan region of the medical device corresponding to each scan, a stitching approach of the medical images collected by the stitching scan, etc.

A movement of a movable component of the medical device may cause a change in the scan area of the medical device. The starting position of the movable component corresponding to a scan refers to a position of the movable component when a first scan of the stitching scan is performed. The ending position of the movable component refers to a position of the movable component when a last scan of the stitching scan is performed. In some embodiments, if the scan is a non-stitching scan (e.g., includes a single scan directed to a specific part of the subject), the starting position the ending position of the movable component may be a same position. In other words, the movable component may not need to be moved during the non-stitching scan. In some embodiments, the count of the scans, the scan region of the medical device corresponding to each scan, the stitching approach of the images collected by the stitching scan, etc. may be determined based on the starting position and the ending position of the movable component.

In some embodiments, the scan of the subject may be a tomography scan (e.g., a CT scan), and the one or more acquisition parameters of the medical device may include a tomography scan protocol relating to the tomography scan. As used herein, the tomography scan may be implemented by performing one or more cross-sectional scans on one or more slices of the subject. The tomography scan protocol may include acquisition parameter(s), such as a count of the slice(s), a thickness and a position of each of the slice(s), a distance between two adjacent slices, a radiation dose, a tube voltage, or the like, or any combination thereof.

In some embodiments, a preset value of an acquisition parameter may be set manually by a user according to experience. In some embodiments, a preset value of an acquisition parameter may be set by the processing device 120A based on a plurality of sample scans.

In some embodiments, the processing device 120A may select a preset scan protocol according to the region of the subject to be scanned. The preset scan protocol may include the one or more preset values of the one or more acquisition parameters. For example, if the region of the subject to be scanned is the chest of the subject, the processing device 120A may select a preset scan protocol corresponding to a chest scan. The one or more preset values of the one or more acquisition parameters determined based on the preset scan protocol may have a limited accuracy because they are determined for the general public without considering the actual feature of the subject.

In 720, the processing device 120A (e.g., the determination module 404) may determine, based on image data of the subject captured by an image capturing device, morphological information of the subject.

In some embodiments, the morphological information of the subject may include height information, facial feature information, thickness information, body width information, bone joint information, or the like, or any combination thereof, of the subject. The facial feature information of the subject may reflect an orientation (e.g., facing or facing away from a radiation source) of the subject. The thickness information of the subject may reflect a distance that radiation rays need to pass through in the subject during the scan. For example, if the region of the subject to be scanned is the chest of the subject, the thickness information of the subject may include a distance between the front chest and the back of the subject. The body width information may reflect a width of the body of the subject (or the region to be scanned). In some embodiments, the thickness information and the body width information of the subject may be determined based on the image data, the height, and/or the weight of the subject. The bone joint information may include a name, a position, and/or a joint angle of each of one or more bone joints of the subject. For example, the bone joint(s) may include the head, shoulders (e.g., the left shoulder, the right shoulder), elbows (e.g., the left elbow, the right elbow), wrists (e.g., the left wrist, the right wrist), hands (e.g., the left hand, the right hand), the hip, knees (e.g., the left knee, the right knee), ankles (e.g., the left ankle, the right ankle), feet (e.g., the left foot, the right foot), or the like, or any combination thereof.

In some embodiments, the image data of the subject may be captured by an image capturing device, such as the image capturing device 160 mounted in an examination room. In some embodiments, the processing device 120A may obtain the image data of the subject using one or more image capturing devices (e.g., one or more 3D cameras) at different positions (e.g., in front of, behind, a side of the subject, etc.). In some embodiments, the image capturing device may obtain the image data of the subject after the subject has finished the positioning procedure or before the subject has finished the positioning procedure (e.g., when the subject enters the examination room).

In some embodiments, the image data of the subject may include 3D image data (or referred to as depth information) captured by a 3D camera (also referred to as a depth camera). The processing device 120A may determine the morphological information of the subject based on the 3D image data (or the depth information) according to an image analysis algorithm (e.g., an image segmentation algorithm). In some embodiments, the processing device 120A may directly obtain the morphological information of the subject from a 3D camera (e.g., a structured light 3D camera, a time-of-flight (TOF) camera, a binocular stereo vision camera, etc.).

In some embodiments, the processing device 120A may determine part or all of morphological information of the subject in other ways. For example, the processing device 120A may obtain the morphological information of the subject that is input by the subject or a user via a terminal. As another example, the processing device 120A may retrieve the morphological information of the subject from a database based on identity information of the subject.

In some embodiments, the processing device 120A may determine the morphological information of the subject by processing the image data of the subject using a morphological information determination model. The morphological information determination model may be configured to extract feature information (e.g., bone joint information, surface profile information, etc.) of the subject based on the image data of the subject and determine the morphological information of the subject based on the feature information of the subject. Merely by way of example, the image data of the subject may be input into the morphological information determination model, and the morphological information determination model may output the morphological information of the subject or information that can be used to determine the morphological information.

In some embodiments, the processing device 120A may obtain the morphological information determination model from one or more components of the medical system 100 (e.g., the storage device 130, the terminals(s) 140) or an external source via a network (e.g., the network 150). For example, the morphological information determination model may be previously trained by a computing device (e.g., the processing device 120B), and stored in a storage device (e.g., the storage device 130, the storage device 220, and/or the storage 390) of the medical system 100. The processing device 120A may access the storage device and retrieve the morphological information determination model. In some embodiments, the morphological information determination model may be generated according to a machine learning algorithm as described elsewhere in this disclosure (e.g., FIG. 4B and the relevant descriptions).

For example, the morphological information determination model may be trained according to a supervised learning algorithm by the processing device 120B or another computing device (e.g., a computing device of a vendor of the morphological information determination model). The processing device 120B may obtain one or more training samples and a preliminary model. Each training sample may include sample image data of a sample subject and reference morphological information of the sample subject. The reference morphological information may be provided or confirmed by a user and used as ground truth morphological information.

The training of the preliminary model may include one or more iterations to iteratively update model parameters of the preliminary model based on the training sample(s) until a termination condition is satisfied in a certain iteration. Exemplary termination conditions may include that the value of a loss function obtained in the certain iteration is less than a threshold, that a certain count of iterations has been performed, that the loss function converges such that the difference of the values of the loss function obtained in a previous iteration and the current iteration is within a threshold value, etc. The loss function may be used to measure a discrepancy between morphological information of the sample subject predicted by the preliminary model in an iteration and the reference morphological information of the sample subject. Exemplary loss functions may include a focal loss function, a log loss function, a cross-entropy loss, a Dice ratio, or the like. If the termination condition is not satisfied in the current iteration, the processing device 120B may further update the preliminary model to be used in a next iteration according to, for example, a backpropagation algorithm. If the termination condition is satisfied in the current iteration, the processing device 120B may designate the preliminary model in the current iteration as the morphological information determination model.

In 730, the processing device 120A (e.g., the determination module 404) may determine, based on the one or more preset values of the one or more acquisition parameters and the morphological information of the subject, one or more values of the one or more acquisition parameters of the medical device.

In some embodiments, for each of the one or more acquisition parameters, the processing device 120A may determine the value of the acquisition parameter based on the preset value of the acquisition parameter and the morphological information of the subject. For example, if the scan is a chest scan during which the subject holds an upright posture, and the height of the subject is 1.90 meters (which is higher than the general public (e.g., 1.70 meters)), the processing device 120A may increase the preset value of the height of the gantry or the radiation source according to the height of the subject. As another example, if the thickness of the region of the subject to be scanned is greater than the general public, the processing device 120A may increase (e.g., proportionally increase) the preset value of an exposure parameter (e.g., the tube voltage and/or tube current) of the high-voltage generator according to the thickness of the region of the subject to be scanned. As still another example, if the body width of the subject is greater than the general public, the processing device 120A may increase the preset value of the size of the light field of the beam limiting device according to the body width of the subject so that the radiation rays may cover the region of the subject to be scanned.

In some embodiments, the processing device 120A may determine the value(s) of the acquisition parameter(s) using an acquisition parameter determination model. Merely by way of example, the image data, the region to be scanned, the morphological information, or the like, or any combination thereof, of the subject may be input into the acquisition parameter determination model, and the acquisition parameter determination model may output the value(s) of the acquisition parameter(s) or information that can be used to determine the value(s) of the acquisition parameter(s).

In some embodiments, the obtaining of acquisition parameter determination model may be performed in a similar manner as that of the morphological information determination model as described elsewhere in this disclosure, and the descriptions thereof are not repeated here.

In some embodiments, if the scan is a stitching scan, the morphological information of the subject may include the bone joint information of the subject, and the processing device 120A may determine the starting position and the ending position of a movement component of the medical device based on the region of the subject to be scanned and the bone joint information of the subject. For example, the region of the subject to be scanned may be a region between the neck and the ankles of the subject. The processing device 120A may determine a position corresponding to the neck of the subject as the starting position of the movement component and a position corresponding to the ankles of the subject as the ending position of the movement component according to the bone joint information of the subject. A distance between the starting position and the ending position of the movable component is also referred to as a moving distance hereinafter.

The processing device 120A may determine the stitching scan protocol based on the starting position and the ending position of the movement component. Since the heights of different subjects are different, for different subjects with a same region to be scanned, the moving distances of the movement component determined based on bone joint information of different subjects are different. The processing device 120A may determine the count of the scans, the scan region of the medical device corresponding to each scan, the stitching approach of the images collected by the stitching scan, etc., based on the starting position, the ending position, and the moving distance of the movable component.

In some embodiments, for each scan of the stitching scan, the processing device 120A may determine a region of the subject to be scanned in the scan based on the scan region of the medical device corresponding to the scan, and morphological information of the region of the subject to be scanned in the scan. The processing device 120A may determine one or more values of the one or more acquisition parameters corresponding to the scan based on the region of the subject to be scanned and the morphological information of the region of the subject to be scanned in the scan.

In 740, the processing device 120A (e.g., the control module 408) may cause the medical device to perform a scan on the subject based on the one or more values of the one or more acquisition parameters.

In some embodiments, before the scan is performed, the processing device 120A may determine the morphological information of the subject continuously or intermittently (e.g., periodically). The processing device 120A may determine whether the value of an acquisition parameter (e.g., the starting position of a movement component) meets the requirements of the scan based on the determined morphological information. The requirements of the scan may include one or more conditions that the medical device and/or the subject need to meet when the medical device performs the scan on the subject. For example, the requirements of the scan may include that the region of the subject to be scanned needs to be within the light field of the medical device. For example, the processing device 120A may determine whether the value of an acquisition parameter meets the requirements of the scan based on the bone joint information (e.g., a position, a joint angle of a bone joint).

In some embodiments, the processing device 120A may determine whether the value of an acquisition parameter meets the requirements of the scan based on a current posture of the subject. For example, the processing device 120A may determine whether the value of an acquisition parameter meets the requirements of the scan based on a difference between the current posture of the subject and a reference posture.

In response to determining that the value of the acquisition parameter cannot meet the requirements of the scan, the processing device 120A may adjust the value of the acquisition parameter. In some embodiments, when the one or more values of the one or more acquisition parameters do not meet the requirements of the scan due to movements of the subject, the processing device 120A may reperform operations 720 and 730 to redetermine the one or more values of the one or more acquisition parameters of the medical device until the requirements of the scan are met.

In some embodiments, when the one or more acquisition parameters of the medical device still meet the requirements of the scan, the processing device 120A may cause the medical device to perform the scan on the region of the subject to be scanned based on the one or more acquisition parameters.

In some embodiments, as described in connection with operation 540, the scan may be performed based on a determination result that a positioning procedure of the subject has been finished, status information of the medical device, a starting signal of the scan, and the one or more acquisition parameters of the medical device.

Conventionally, a medical device performs a scan on a subject according to preset value(s) of one or more acquisition parameters. If the scan performed according to the preset value(s) of the one or more acquisition parameters cannot meet requirements of a user (e.g., a doctor), for example, one or more images collected by the scan have a low image quality and do not meet diagnosis requirements of the user, the user may need to manually adjust the preset value(s) of the one or more acquisition parameters according to experience.

In the process 700, the processing device 120A may automatically or partially automatically determine the one or more values of the one or more acquisition parameters of the medical device based on the morphological information of the subject and the one or more preset values of the one or more acquisition parameters, which is time-saving, more efficient, and more accurate (e.g., insusceptible to human error or subjectivity). In addition, the scan performed based on the one or more acquisition parameters obtained according to the process 700 is more accurate, thereby reducing unnecessary radiation rays.

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 700 may be accomplished with one or more additional operations not described and/or without one or more of the operations discussed above. For example, operation 740 may be omitted, that is, the process 700 may be used to determine the one or more values of the one or more acquisition parameters of the medical device.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer-readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations thereof, are not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A method for medical imaging, implemented on a computing device having one or more processors and one or more storage devices, the method comprising:
   determining, based on personal information of a subject, positioning guidance information;
   causing the positioning guidance information to be displayed to the subject;
   obtaining a posture of the subject based on first image data of the subject;
   generating a first determination result indicating that a positioning procedure of the subject has been finished based on the personal information and the posture of the subject;
   generating a second determination result indicating that the subject has remained in a preset static mode or a preset motion mode for a preset time by tracking a motion of one or more feature points or one or more regions of interest of the subject based on second image data of the subject, the first image data and the second image data being a same set of image data or different sets of image data captured by one or more imaging capturing devices, a posture of the subject being unchanged in the preset static mode, and a motion amplitude of the subject being less than a first threshold in the preset motion mode;
   prompting the subject to send a starting signal indicating that a scan on the subject can be started based on the first determination result and the second determination result; and
   causing the medical device to start performing the scan on the subject after the starting signal of the scan is received.

2. The method of claim 1, further comprising:
   the display form of the positioning guidance information includes one or more of a voice prompt, a video display, an image display, or a text display.

3. The method of claim 1, wherein the generating a first determination result indicating that a positioning procedure of the subject has been finished based on the personal information and the posture of the subject comprises:
   determining, based on the personal information of the subject, a reference posture of the subject; and
   generating the first determination result indicating that the positioning procedure of the subject has been finished based on a comparison between the posture and the reference posture of the subject.

4. The method of claim 1, further comprising:
   determining, based on third image data of the subject captured by the one or more image capturing devices, morphological information of the subject; and
   determining, based on the morphological information of the subject, one or more values of one or more acquisition parameters of the medical device, wherein the scan is performed based on the one or more values of the one or more acquisition parameters.

5. The method of claim 4, wherein the determining, based on the morphological information of the subject, one or more values of the one or more acquisition parameters of the medical device comprises:
   determining, based on a region of the subject to be scanned, one or more preset values of the one or more acquisition parameters of the medical device; and
   determining the one or more values of the one or more acquisition parameters of the medical device based on the one or more preset values of the one or more acquisition parameters and the morphological information of the subject.

6. The method of claim 4, wherein the scan is a stitching scan or a tomography scan, and the one or more acquisition parameters of the medical device include a stitching scan protocol relating to the stitching scan or a tomography scan protocol relating to the tomography scan.

7. The method of claim 6, wherein the scan is the stitching scan, the morphological information of the subject includes bone joint information of the subject, and the determining, based on the morphological information of the subject, one or more values of one or more acquisition parameters of the medical device comprises:
   determining the stitching scan protocol based on the bone joint information of the subject.

8. A system for medical imaging, comprising:
   one or more storage devices including a set of instructions; and
   one or more processors configured to communicate with the one or more storage devices, wherein when executing the set of instructions, the one or more processors are configured to direct the system to perform operations including:
      determining, based on personal information of a subject, positioning guidance information;
      causing the positioning guidance information to be displayed to the subject;

obtaining a posture of the subject based on first image data of the subject;

generating a first determination result indicating that a positioning procedure of the subject has been finished based on the personal information and the posture of the subject;

generating a second determination result indicating that the subject has remained in a preset static mode or a preset motion mode for a preset time by tracking a motion of one or more feature points or one or more regions of interest of the subject based on second image data of the subject, the first image data and the second image data being a same set of image data or different sets of image data captured by one or more imaging capturing devices, a posture of the subject being unchanged in the preset static mode, and a motion amplitude of the subject being less than a first threshold in the preset motion mode;

prompting the subject to send a starting signal indicating that a scan on the subject can be started based on the first determination result and the second determination result; and causing the medical device to start performing the scan on the subject after the starting signal of the scan is received.

9. The system of claim 8, wherein the generating a first determination result indicating that a positioning procedure of the subject has been finished based on the personal information and the posture of the subject comprises:

determining, based on the personal information of the subject, a reference posture of the subject; and generating the first determination result indicating that the positioning procedure of the subject has been finished based on a comparison between the posture and the reference posture of the subject.

10. The system of claim 8, wherein the operations further include:

determining, based on third image data of the subject captured the one or more image capturing devices, morphological information of the subject; and determining, based on the morphological information of the subject, one or more values of one or more acquisition parameters of the medical device, wherein the scan is performed based on the one or more values of the one or more acquisition parameters.

11. The system of claim 10, wherein the determining, based on the morphological information of the subject, one or more values of the one or more acquisition parameters of the medical device comprises:

determining, based on a region of the subject to be scanned, one or more preset values of the one or more acquisition parameters of the medical device; and determining the one or more values of the one or more acquisition parameters of the medical device based on the one or more preset values of the one or more acquisition parameters and the morphological information of the subject.

12. The system of claim 10, wherein the scan is a stitching scan or a tomography scan, and the one or more acquisition parameters of the medical device include a stitching scan protocol relating to the stitching scan or a tomography scan protocol relating to the tomography scan.

13. A non-transitory computer readable medium, comprising a set of instructions for medical imaging, wherein when executed by at least one processor of a computing device, the set of instructions direct the computing device to perform a method, the method comprising:

determining, based on personal information of a subject, positioning guidance information;

causing the positioning guidance information to be displayed to the subject;

obtaining a posture of the subject based on first image data of the subject;

generating a first determination result indicating that a positioning procedure of the subject has been finished based on the personal information and the posture of the subject;

generating a second determination result indicating that the subject has remained in a preset static mode or a preset motion mode for a preset time by tracking a motion of one or more feature points or one or more regions of interest of the subject based on second image data of the subject, the first image data and the second image data being a same set of image data or different sets of image data captured by one or more imaging capturing devices, a posture of the subject being unchanged in the preset static mode, and a motion amplitude of the subject being less than a first threshold in the preset motion mode;

prompting the subject to send a starting signal indicating that a scan on the subject can be started based on the first determination result and the second determination result; and causing the medical device to start performing the scan on the subject after the starting signal of the scan is received.

* * * * *